United States Patent [19]

Müller-Lierheim

[11] Patent Number: 4,895,896
[45] Date of Patent: Jan. 23, 1990

[54] CONTACT LENS HAVING IMPROVED EYE COMPATIBILITY

[76] Inventor: Wolfgang Müller-Lierheim, Lichtweg 5, D-8032 Grafelfing, Fed. Rep. of Germany

[21] Appl. No.: 85,487

[22] Filed: Aug. 14, 1987

[30] Foreign Application Priority Data

Aug. 18, 1986 [DE] Fed. Rep. of Germany ....... 3627937
Jul. 23, 1987 [EP] European Pat. Off. ........ 87110671.2

[51] Int. Cl.$^4$ .......................... G02C 7/04; G02B 1/04
[52] U.S. Cl. .................................. 525/54.1; 530/811; 530/812; 530/815; 523/106; 351/160 R; 351/160 H
[58] Field of Search ............... 525/54.1; 530/810, 811, 530/812, 815; 523/106; 351/160 R, 160 H

[56] References Cited

U.S. PATENT DOCUMENTS 4,560,504 12/1985 Arnold ................................. 530/811
4,609,707 9/1986 Nowinski et al. .................. 525/54.1
4,737,544 4/1988 McCain et al. ..................... 525/54.1

FOREIGN PATENT DOCUMENTS 0088606 9/1983 European Pat. Off. .
8607264 12/1986 European Pat. Off. .

*Primary Examiner*—John Kight
*Assistant Examiner*—Nathan M. Nutter
*Attorney, Agent, or Firm*—Fleit, Jacobson, Cohn, Price, Holman & Stern

[57] ABSTRACT

Contact lens comprising an eye-compatible surface on which monoclonal antibodies or fragments of antibodies are immobilized, the N-terminal ends of which are directed against mucous substances of the human ocular tear film.

12 Claims, No Drawings

CONTACT LENS HAVING IMPROVED EYE COMPATIBILITY

This application is related to U.S. Application Ser. No. 085,228, filed Aug. 13, 1987 and now U.S. Pat. No. 4,828,563, which is a continuation-in-part of U.S. Application Ser. No. 875,546, entitled IMPLANT, filed June 18, 1986, now abandoned, and to U.S. Application Ser. No. 122,504, filed Nov. 18, 1987, which is a continuation-in-part of U.S. Application Ser. No. 938,838, entitled CARRIER BODY BIOACTIVATED BY ANTIBODIES COVALENT BONDED TO THE SURFACE THEREOF, filed Dec. 8, 1986, now abandoned.

BACKGROUND OF THE INVENTION

This invention relates generally to a contact lens with improved eye-compatibility. Contact lenses usually are made of inert, non-toxic, optically clear, and schlieren-free plastic materials. The contact lens material may be hard contact lens material, e.g. polymethyl methacrylate, or else soft contact lens material, e.g., polyhydroxy ethylmethacrylate, or polyethylene glycoldimethacrylate. Thin contact lenses made of gas-permeable polymers are preferably in use at this time as they minimize the effect on the metabolism of the underlying cornea. The selection of suitable polymers or subsequent surface treatment renders the contact lenses wettable by aqueous solutions.

The main problems of wearing contact lenses are:
mechanical irritation of eyelid and cornea,
contamination, cleaning, and disinfection of the contact lens; and
reduction of tear-film stability.

Depending on the type of contact lens, a wearer can get used to the mechanical irritation within a period ranging from a few hours to no more than weeks.

The second problem, contamination of the contact lens by non-specific adsorption of lipids, proteins, mucins, and salts of the tear-film as well as by other molecules and particles, including microorganisms, is commonly taken care of by regular cleaning and disinfection. Detergents, as well as proteolytic enzymes, are used for cleaning the contact lens. Proteins that are not removed completely from the contact lens frequently are denatured during cleaning and chemical or heat disinfection and can cause allergic reactions in the conjuctiva of the contact-lens wearer.

As for the third problem, reduction of tear-film stability, it helps to understand the structure of the tear film. The human ocular tear film consists—in simplified presentation—of three layers:
a mucin layer that smoothes the rough surface of the corneal epithelium and renders the hydrophobic corneal epithelium wettable;
an aqueous phase; and
a lipid layer that insulates the aqueous phase from the surrounding air.

The lipid layer of the tear film prevents rapid evaporation of the aqueous phase and excessively rapid cooling of the cornea. The wearing of conventional contact lenses causes a reduction of the stability of the tear film and consequently a more rapid evaporation of the aqueous phase of the tear film. For that reason, contact lens wearers frequently suffer from dry eyes and often must resort to eye drops to relieve the problem. Moreover, the instability of the tear film leads, in many cases, to non-tolerance of the contact lens.

SUMMARY OF THE INVENTION

Consequently, it is an aim of this invention to create a contact lens with a surface whose eye-compatibility is improved so as to be adapted as closely as possible to the properties of the conjunctiva of the eye.

In accordance with the invention, this goal is achieved by immobilizing, on the surface of the contact lens, monoclonal antibodies or antibody fragments, the N-terminal ends of which are directed against mucous substances of the human ocular tear film. The epitopes of these mucous substances, which are secreted by the conjunctival epithelium, are thereby selectively bound to the surface of the contact lens.

As the antibodies and/or antibody fragments preferably have a maximum binding capability at the pH-value of the lachrymal fluid, i.e., at approximately 7.0 to 7.5, the affinity to the bound molecules is reduced, in the case of a pH-change, to such an extent that they desorb, resulting in a gentle cleaning of the contact lens.

In this way, the goal of the invention is achieved: a mucous layer is produced on the surface of the contact lens that establishes the desired wettability by the tear film. Since the antibodies and/or antibody fragments are created, in the area of the N-terminal ends, so as to be hydrophobic, the surface of the body of the contact lens has the same properties as the epithelium of the cornea while, at the same time, the mucous layer which is bound by the antibodies to the surface of the body of the lens, brings about good wettability by the tear fluid.

DESCRIPTION OF PREFERRED EMBODIMENT

In a preferred embodiment of the invention, antibodies and/or antibody fragments are bound to the surface of the body of the contact lens, that adsorb plasma proteins of the human ocular tear film on their N-terminal ends. Those proteins which contain, among other substances, albumin and alpha-, beta-, gamma globulin as well as lysozyme (Chien-chyou W. Chao and Stuart I. Brown, *Macromolecular components of human ocular mucus*, in *The preocular tear film*, pp. 331–340. Lubbock, TX, Dry Eye Institute, 1986), are a main component of the mucuous layer.

The plasma proteins, in particular albumin, serve as sliding substances and as wetting agents in the tear fluid. The mucuous layer on the human eye largely consists of mucosubstances (some 40%) with a molecular weight of more than $10^5$ amu and of the plasma proteins (some 60%) with an atomic weight of less than $10^5$ amu. The mucosubstances are largely complex glycoconjugates consisting of glycoproteins and proteoglycans (Table 1, p. 333 of the aforementioned publication).

Conventional hybridoma techniques are suitable for obtaining the antibodies. To that end, the monoclonal antibodies are obtained from hybridoma cells that are fusion products of mouse-spleen cells with myeloma cells. The mouse-spleens come from animals—preferably Balb/c mice—that have been immunized with an appropriate mucous substance, such as albumin, beta globulin, lysozyme, alpha globulin and gamma globulin (Lowry et. al, JBC 193: 265).

The mice are immunized once a month, over a period of four to six months, with the chosen mucous substance until a sufficient antibody titer, greater than or equal to 1:10,000, is observed with the aid of the ELISA (enzyme linked immunosorbent technique)-technique. A booster injection of the appropriate mucous substance is then administered. The mouse is killed and the spleen cells, which have been removed in a sterile manner, are fused with myeloma cells (e.g. cell line P3X63-Ag8.653.ATCC CRL 1580).

The hybridization products obtained are selected in a HAT-standard selective medium (hypoxanthine, aminopterin, thymidine). Primary cultures that present a positive reaction in the supernatant are cloned. The monoclonal antibodies of those clones are tested for specificity, particularly in regard to cross reactions with lipids in the tear film and with germs on the conjunctiva. Among the microorganisms against which cross-reactivity of the monoclonal antibodies is tested, are the following which may be present in ocular fluid or inhabit the conjunctiva:

*Staphylococcus aureus*
*Corynebacterium xerosis*
Streptococcus
*Bacillus subtilis*
*Pseudomonas aeruginosa*
Neisseria
Sarcina
Enterobacteria such as:
  *E. coli*
  *E. freundii*
  Klebsiella
  Proteus spec.
*Aspergillus niger*
*Candida albicans*
Penicillium The selected monoclonal antibodies that are specific for the various mucous substances, are produced, e.g. by ascites production, in the quantities required. To that end, Pristan (2×0.5 ml) is administered to Balb/c-mice at weekly intervals. $5 \times 10^6$ hybridoma cells of the selected clones are applied per mouse. The ascites are obtained after some 11 days.

The antibodies obtained are covalently bound on the surface of conventional contact lens bodies. Of the antibodies and/or antibody fragments that are directed against plasma proteins, there are directed some
25 to 30% against albumin
25 to 30% against beta globulin
25 to 30% against lysozyme
3 to 10% against alpha globulin
3 to 6% against gamma globulin.

The surfaces of the contact lens bodies comprise linkage-active chemical groups that have been formed largely by copolymerization of suitable monomers or oligomers. They may be —SH, —OH, —NH$_2$, —C≡N, or

groups. Oxirane groups are preferred for the immobilization of the antibodies on the surface of the contact lens.

The following examples illustrate the immobilization of the antibodies on the surface of the contact lens:

EXAMPLE 1

Carrier surfaces carrying amino groups may be activated for example with thiophosgene. An isothiocyanate is produced in that case on the carrier as the activating species. The routines involved are shown below.

(a) Carrier Activation

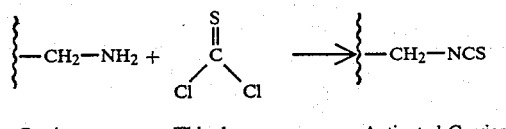

(b) Antibody Immobilization

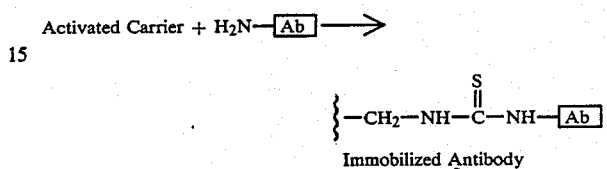

EXAMPLE 2

A wide reaction spectrum is afforded by the epichlorhydrin method. Therein, the carrier surface is spiked by means of epichlorhydrin with oxirane group-bearing spacers. The epoxy groups, which are under ring tension, may be opened under very mild reaction conditions nucleophilically with thiol, hydroxyl, or amino groups.

(a) Carrier Activation

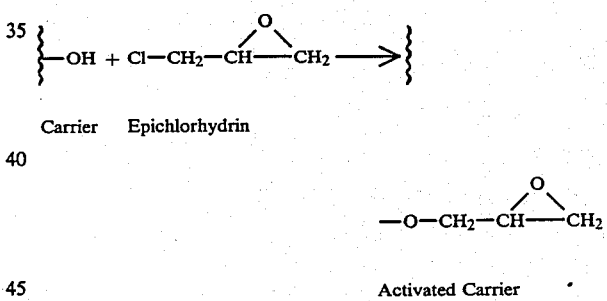

(b) Antibody Immobilization

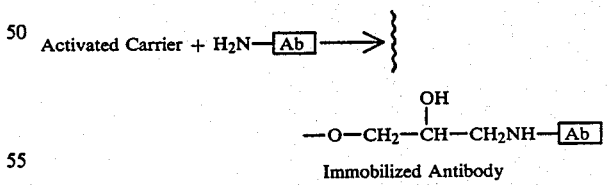

EXAMPLE 3

The effectiveness of an immobilization action depends not only on the choice of the linking method but also the carrier-protein spacing.

Such aspects are taken into consideration, for example, by the biepoxyoxirane method. In that method, one oxirane group is used for anchoring to the carrier and the second is used for fixing the protein.

(a) Carrier Activation

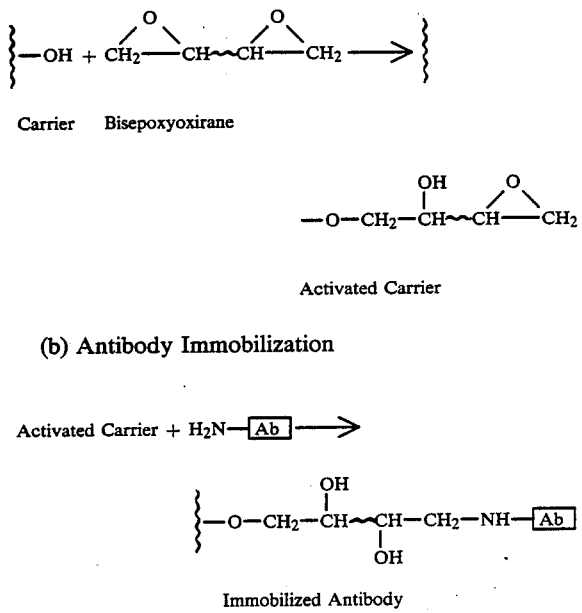

Carrier   Bisepoxyoxirane

Activated Carrier (b) Antibody Immobilization

Activated Carrier + H₂N—[Ab] ⟶

Immobilized Antibody

What is claimed is:

1. Contact lens comprising a lens body with a surface having monoclonal antibodies or fragments of antibodies immobilized thereon, the N-terminal ends of said immobilized antibodies or antibody fragments being directed against mucous substances which are secreted by the epithelium of the conjunctiva of a human eye so that a mucous layer is formed on the surface of the lens body when the contact lens is worn on the human eye.

2. Contact lens in accordance with claim 1, wherein said antibodies and/or antibody fragments have a maximum binding capability at the pH of lachrymal fluid, about 7.0 to 7.5.

3. Contact lens in accordance with claim 1, wherein the area of the N-terminal ends of the antibodies and/or antibody fragments is hydrophobic.

4. Contact lens in accordace with claim 1, wherein said antibodies and/or antibody fragments do not cross-react with any lipids of the human ocular tear film.

5. Contact lens in accordance with claim 1, wherein said antibodies and/or antibody fragments are directed against plasma proteins of the human ocular tear film.

6. Contact lens in accordance with claim 5, wherein said antibodies and/or antibody fragments are directed against albumin.

7. Contact lens in accordance with claim 5, wherein, of the antibodies and/or antibody fragments that are directed against plasma proteins, there are directed some
   25 to 30% against albumin
   25 to 30% against beta globulin
   20 to 30% against lysozyme
   3 to 10% against alpha globulin
   3 to 6% against gamma globulin.

8. Contact lens in accordance with claim 1, wherein said antibodies and/or antibody fragments are directed against glyco-conjugates of the human ocular tear film.

9. Contact lens in accordance with claim 1, wherein said antibodies and/or antibody fragments are covalently bound to the surface of the contact lens.

10. Contact lens is accordance with claim 1, wherein the surface of the body of the lens is activated by way of —SH, —OH, —NH₂, —C≡N, or

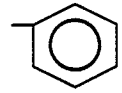

groups, and the antibodies and/or antibody fragments are covalently bound to the surface of the lens by way of these groups.

11. Contact lens in accordance with claim 1, wherein the active chemical groups on the surface of the body of the lens are formed by polymerization of suitable monomers or oligomers.

12. Contact lens in accordance with claim 1, wherein said antibodies and/or antibody fragments do not cross-react with any germs occurring on the human conjuctiva or in the tear ducts.

* * * * *